United States Patent [19]

Nazarov et al.

[11] 3,988,354
[45] Oct. 26, 1976

[54] METHOD OF ISOLATING GRANULAR ANTHRAQUINONE FROM ANTHRAQUINONE PRODUCTION PROCESS GASES

[76] Inventors: Vladimir Georgievich Nazarov, ulitsa Belinskogo, 152, korpus 2, kv. 32; Vladimir Konstantinovich Nepokrytykh, ulitsa Belorechenskaya, 36, kv. 118, both of Sverdlovsk; Ljubov Markovna Vasilevskaya, ulitsa Ivanova, 30, kv. 4, Voroshilovgradskava oblast, Rubezhnoe; Natalya Dmitrievna Rusyanova, ulitsa 8 Marta, 7, kv. 3; Natalya Borisovna Volgina, ulitsa Gagarina 47, kv. 12, both of Sverdlovsk; Vitaly Fedorovich Chernyshev, ulitsa Lenina, 48, kv. 89, Sverdlovsk; Nina Alexandrovna Chetverikova, ulitsa Samoletnaya, 3, korpus 1, kv. 42, Sverdlovsk, Uktus; Alexandr Stepanovich Kostromin, ulitsa Shartashskaya, 10, kv. 38, Sverdlovsk, all of U.S.S.R.

[22] Filed: Jan. 13, 1975

[21] Appl. No.: 540,700

Related U.S. Application Data

[63] Continuation of Ser. No. 376,436, July 5, 1973, abandoned.

[52] U.S. Cl. .............................. 260/369; 260/385; 260/706
[51] Int. Cl.$^2$ ......................................... C07C 49/68
[58] Field of Search ................. 260/385, 369, 346.7, 260/706

[56] References Cited
UNITED STATES PATENTS

| | | | |
|---|---|---|---|
| 2,607,440 | 8/1952 | Lewis | 260/346.7 |
| 3,113,140 | 12/1963 | Matz et al. | 260/369 |

FOREIGN PATENTS OR APPLICATIONS
346,207   6/1960   Switzerland

OTHER PUBLICATIONS
Nazarov et al. Chem. Abstracts 76 (1972) No. 129746.

*Primary Examiner*—Arthur P. Demers
*Attorney, Agent, or Firm*—Holman & Stern

[57] ABSTRACT

A method of isolating granular anthraquinone from anthraquinone production process gases which consists of passing said gasses through a fluidized bed of anthraquinone granules at a temperature of 110° to 160° C.

While the gas is being passed through the fluidized bed, the anthraquinone vapors are condensed on the granules which are destroyed as fast as the layer of the condensed anthraquinone is grown thereon with the formation of new granules, and whereon anthraquinone condensation occurs as well. Part of the granules of the anthraquinone are isolated from the fluidized bed as the finished product.

3 Claims, No Drawings

METHOD OF ISOLATING GRANULAR ANTHRAQUINONE FROM ANTHRAQUINONE PRODUCTION PROCESS GASES

This is a continuation of application Ser. No. 376,436 filed July 5, 1973, now abandoned.

The present invention relates generally to the sphere of organic synthesis of anthraquinone, and has particular reference to a method aimed at the isolation of granular anthraquinone from anthraquinone production process gases.

Anthraquinone is known to be the raw stock for the synthesis of high-quality dyestuffs and maybe obtained on an industrial scale by being synthesized from phthalic anhydride and benzene, or by vapor-phase catalytic oxidation of anthracene. Anthraquinone as obtained by the known conventional methods is essentially a wool-like or powdery product having a bulk weight of from 0.25 to 0.35 g/m$^3$, and consisting of lemon-yellow coloured needle-like crystals. The product contains not less than 98 per cent of the main substance.

The known production technique for anthraquinone involves the stage of isolating same from its process gases. Such gasses are contact gases from the vapor-phase anthracene oxidation process and those of the sublimation anthraquinone purification, containing anthraquinone vapors and the concomitant admixtures of the vapors of the by-products and the raw stock.

It is known to use heretofore in industrial practice some methods of isolating anthraquinone from its process gases by a fractional sublimating condensation on the condenser walls, or by sublimating condensation of vapors in the gaseous volume of the process gas by cooling, followed by the isolation of the anthraquinone dust in dust separators.

The disadvantages inherent in the known methods of isolating anthraquinone from process gases are as follows.

1. The low heat transfer itensity of the process gas to the condensation surface involves the use of numerous parallel or series-connected surface condensers, which involves large capital investments and complicates servicing of the operative plants. The effective heat-transfer of the condensers surface cools inadequately, for which reason a considerable proportion of the admixtures of the organic side-products of the reaction and that of the original stock get condensed along with anthraquinone. Due to this fact, the effective heat-transfer surfaces of the condensers gradually become encrusted with solid deposits of the resinified anthraquinone and the condensed admixtures of the side products, which deposits must be removed manually thus interrupting the continuous production process.

2. The sublimating condensation of anthraquinone in the gaseous volume of the process gas under cooling involves the use of complicated dust separation devices, and the yield of the finished product is reduced due to high losses when the exit gases leave the dust separators. Moreover, the abnormally high anthraquinone dust content in the exit gases hampers the sanitary treatment of same before their being discharged into the atmosphere. The surfaces of the dust separation devices that are in contact with the process gases become encrusted with solid deposits of the resinified anthraquinone and the condensed admixtures of the side products. Said deposits have to be removed by hand, thus discontinuing the continuous production process.

3. The wool-like or powdery anthraquinone having a low bulk weight is not loose and can therefore be neither proportioned nor prepacked by any automated and power-assisted means. That is why the anthraquinone is now prepacked and proportioned manually both in production and in utilization. No methods of producing granular qnthraquinone enabling automation of the process have been heretofore proposed.

It is therefore an object of the present invention to develop a method of isolating anthraquinone from anthraquinone production process gases that would enable the process to occur in an automated cycle in a single stage.

It is another object of the present invention to produce granular anthraquinone suitable for being proportioned, prepacked and handled with the use of mechanized means at the stage of production and utilization thereof.

It is still another object of the present invention to increase the percentage of the anthraquinone yield from its process gases and to diminish its losses with respect to the exit gases discharged into the atmosphere.

It is yet still another object of the present invention to provide a method of isolating anthraquinone from the contact gases of the vapor-phase oxidation containing the vapors of two products, viz., anthraquinone and phthalic anhydride with the simultaneous production of the latter.

Said objects are accomplished in a method of isolating anthraquinone from anthraquinone production process gases which, according to the invention, consists in that said gases are passed through a fluidized bed of anthraquinone granules at a temperature for said bed selected within 110° to 160° C depending upon the composition and amount of the admixtures in said gases and the requirements imposed upon the quality of the product, with the result being that the anthraquinone vapors are condensed on the granules, with a part of the latter being destroyed as fast as the layer of the condensed anthraquinone is grown thereon in order to form new granules whereon anthraquinone condensation occurs as well, and after which the granules taken in an amount corresponding to the quantity of the condensed anthraquinone are isolated from said fluidized bed as the finished product.

The composition of the process gases, wherefrom anthraquinone is isolated, may be diverse and is dependent upon the anthraquinone production method.

The proposed method is instrumental in isolating granular anthraquinone from said diverse-composition anthraquinone production process gases.

Thus, when producing anthraquinone by the vapor-phase anthracene oxidation, the process gas contains, apart from anthraquinone, the unreacted anthracene, as well as carbazole and other admixtures. In such a case anthraquinone is isolated at a fluidized bed temperature of the anthraquinone granules of from 130° to 160° C. When the process occurs at temperatures below 130° C, condensed along side with anthraquinone are also the majority of the carbazole, anthracene and other admixtures which impairs the quality of the main product. On the other hand, carrying out the process at temperatures above the afore-specified ones results in inadmissibly high anthraquinone losses due to its being carried away by vapors evolved by the fluidized bed on account of an incomplete anthraquinone condensation; moreover, subsequent sanitary treatment of the exit gases is made more difficult.

In this case, apart from the fluidized-bed temperature, of great importance is the holding time of the anthraquinone granules in said bed.

When the holding time of the anthraquinone granules in the fluidized bed exceeds 24 hours, part of the admixtures (viz., non-reacted anthracene and carbazole) get resinified, thus impairing the quality of the finished product.

The aforesaid holding time of the anthraquinone granules in the fluidized bed can be obtained by keeping said bed in the condenser at a definite level. In some cases the process gas can also contain, apart from anthraquinone, phthalic anhydride which is likewise to be isolated as a reaction product. Such a case takes place in the vapor-phase oxidation of an antracene-phenanthrene fraction resulting from the processing of coal-tar. The vapor phase oxidation of said fraction produces the process gas which contains the vapors of anthraquinone and phthalic anhydride. Thus, the necessity arises to isolate both of them as the reaction products.

According to the invention, in this case anthraquinone is isolated with the fluid bed of the anthraquinone granules being maintained at a temperature ranging within 110° to 120° C. Keeping the temperature within said limits ensures the production of quality anthraquinone with the content of the main product being up to 98–99 percent, as well as a high quality of phthalic anhydride. The higher-than-specified temperature of the fluidized bed results in the phthalic anhydride becoming contaminated with anthraquinone admixtures, while temperatures dropping below 110° C causes the anthraquinone to be polluted with phthalic anhydride.

The phthalic anhydride vapors that remain uncondensed under the given temperature range are carried out of the fluidized bed. Further on, phthalic anhydride may be isolated from the process gas by resorting to any conventional method, e.g., by sublimation condensation.

Practical application of the proposed method is carried out as follows.

The process proceeds continuously in an apparatus containing a fluidized bed of anthraquinone granules, hereinafter referred to as condenser. The process gas having a temperature of from 230° to 250° C is fed into the condenser through the gas-distribution device located at the bottom of the condenser, said gas passing through the fluidized bed of the anthraquinone granules. The temperature of said fluidized bed is maintained within 110° to 160° C depending upon the composition and amount of the admixtures in the process gas. In order to cool the fluidized bed, a cooling air is passed through the gas-distribution device, or a water-cooled tubular cooler is placed inside said fluidized bed.

The granule size of the fluidized bed exerts no substantial influence upon process efficiency, but the granules having a diameter of from 0.2 to 2.5 mm are most expediently used. However, granules of other size can also be employed.

When the process gas is passed through the fluidized bed of the anthraquinone granules, up to 90–95 percent of anthraquinone contained in said gas condenses on the surface of the granules, with the rest of the 5 to 8 percent of anthraquinone contained in the gaseous volume being carried away as dust from the fluidized bed with the process gas and subsequently isolated in the dust separator provided at the condenser exit. The anthraquinone isolated in the dust separator can be used either as the main product can be returned for a repeated sublimation and condensing. Once past the dust separator the process gas is subjected to sanitary treatment and then discharged into the atmosphere.

The anthraquinone granules in the fluidized bed portion are destroyed as fast as the layer of the condensed anthraquinone is grown thereon to form new granules, whereupon anthraquinone condensation occurs as well.

Part of the granules, in an amount corresponding to the quantity of the condensed anthraquinone, are continuously separated from the condenser as the finished product.

When it is necessary to obtain a product of a desired grading, it can be discharged from the condenser through the separation device which ensures rendering of granules of the required size.

As it becomes evident from the present disclosure, the proposed method is technologically simple and commercially efficient for use on an industrial scale. The method ensures the following advantages.

1. It enables by a few-score the intensification of the process of anthraquinone isolation from the process gases and its being carried out in a single stage on an automatic cycle as a continuous process without resorting to manual labour.

2. It decreases by several times the cost of repair work of the process equipment involved in anthraquinone production and its cleaning it further renders the production process more reliable within a continuous production scale without having any shutdown periods for repair and cleaning of the process equipment.

3. Due to the fact that the main product is granular, conditions are provided for bringing automation and mechanization into process operations concerned, such as conveying, unloading, prepacking, proportioning and the loading of anthraquinone.

4. The method provides for the reduction of anthraquinone losses, as compared to the known methods, at the stage of its isolation from the process gases and makes it possible to easily control the quality characteristics of the product to suit consumers' requirements.

Given hereinbelow are some examples of the practical embodiment of the present invention.

EXAMPLE 1

150 kg of granular anthraquinone are fed into a condenser equipped with a gas distribution device and a product discharge device having particles sizing from 0.2 to 2.5 mm, and 500 $nm^3$/h of air at a temperature of 40°–45° C and 500 $nm^3$/h of the vapor-phase anthracene oxidation process gas are fed through said gas distribution device. The process gas contains 17 $g/nm^3$ of anthraquinone, 0.035 $g/nm^3$ of anthracene and 0.05 $g/nm^3$ of carbazole. The temperature of said gas at the entrance of the condenser is 230° C, with the temperature of the fluidized bed being 140° C. The weight of the granules of the fluidized bed is kept at 140–150 kg which corresponds to a bed height of 400 to 500 mm and ensures that the holding time of the granules in the condenser is not in excess of 24 hours.

The granular finished product is continuously discharged from the condenser at a rate of from 75. to 8 kg/h.

780 kg of granular anthraquinone was produced after 100 hours of continuous operation.

The obtained product has the following weight percentage composition:

| | |
|---|---|
| anthraquinone | − 99.5 |
| carbazole | − 0.20 |
| anthracene | − 0.10 |
| non-identified admixtures | − 0.2 |

The degree of anthraquinone condensation in the fluidized bed is 91.0 percent.

The exit gas leaving the condenser contains, in $g/nm^3$:

| | |
|---|---|
| dust and anthraquinone vapours | − 0.6 |
| anthracene vapors | − 0.01 |
| carbazole vapors | − 0.01 |

Said gas is then fed to the dust separator.

The rate of the gas feed to the dust separator was 1000 $nm^3/h$, and some 40 kg of anthraquinone were additionally isolated from the gas for a 100-hour operating period.

The total degree of anthraquinone extraction in the condenser and dust separator is 96.0 percent.

EXAMPLE 2

A condenser similar to that described in Example 1 containing 150 kg of granular anthraquinone is charged with 500 $nm^3/h$ of air at a temperature of 40° to 45° C and 500 $nm^3/h$ of the process gas of the anthracene-phenanthrene fraction vapor-phase oxidation.

Said process gas contains, in $g/nm^3$:

| | |
|---|---|
| anthraquinone | − 4.5 |
| phthalic anhydride | − 7 |

The temperature of the vapor-gas mixture at the condenser inlet is 23° C, with the temperature of the fluidized bed of anthraquinone granules being maintained within 110° to 120° C. Some 2.0 kg/h of the anthraquinone granules are discharged from the condenser, and contain at least 98 percent of the main product.

The degree of anthraquinone condensation on the granules is 90 percent.

The exit gas from the condenser is fed to the dust separator, wherein 220 g of anthraquinone are further isolated therefrom.

Thus, the total degree of anthraquinone extraction is 99 percent.

The exit gases from the dust separator, contain 7 $g/nm^3$ of phthalic anhydride and about 50 $mg/nm^3$ of anthraquinone which are fed to the phthalic-anhydride isolating system.

EXAMPLE 3

A condenser similar to that described in Example 1 and containing 150 kg of granular anthraquinone, is charged with the process gas of the anthraquinone sublimation purification produced by the synthesis of phthalic anhydride and benzene. Said gas is essentially nitrogen containing 80 $g/nm^3$ of anthraquinone vapors. The condenser exit temperature is 250° C, the gas flow rate being 1000 $nm^3/h$ and the temperature of the fluidized bed of anthraquinone granules equalling 140° to 160° C. The fluidized bed is cooled by means a tubular cooler placed in said fluidized bed and supplied with cold water.

The exit gas from the condenser passes through the filter where anthraquinone dust is separated, whereupon nitrogen is fed to the anthraquinone evaporator to be saturated with the vapors of the latter and is returned to the condenser.

72 kg of granular anthraquinone per hour are rendered from the condenser having a 99.5-percent of its content the main product, while 6 kg of anthraquinone dust are educed from the filter and returned into the evaporator. The resinous high-boiling admixtures with a 10-percent anthraquinone content are eliminated from the evaporator in the liquid state.

The total anthraquinone losses make up about 0.9 percent.

What we claim is:

1. In a method of isolating anthraquinone from a mixture of anthraquinone vapors and non-condensible gases by contacting the vapor-gas mixture with a cooled fluidized bed of anthraquinone granules, the improvement comprising isolating said anthraquinone in granular form by maintaining said fluidized bed at a temperature in the range of 110°–160° C and removing condensed anthraquinone granules thus formed from said fluidized bed at a rate and in a manner that the holding time of said condensed granules in said bed is not in excess of 24 hours.

2. A method, as claimed in claim 1, wherein the temperature of said fluidized bed is maintained within the range 130°–160° C when said non-condensible gases result from vapor-phase anthracene oxidation.

3. A method, as claimed in claim 1, wherein the temperature of said fluidized bed is maintained within the range 110°–120° C when said non-condensible gases contain phthalic anhydride, whereby said phthalic anhydride passes through said bed.

* * * * *